United States Patent
Lippert et al.

(10) Patent No.: US 7,844,335 B2
(45) Date of Patent: Nov. 30, 2010

(54) IMPLANTABLE MEDICAL DEVICE AND METHOD FOR LV CORONARY SINUS LEAD IMPLANT SITE OPTIMIZATION

(75) Inventors: Michael Lippert, Ansbach (DE); Gerald Czygan, Buckenhof (DE); Stefan Paule, Drosendorf (DE)

(73) Assignee: Biotronik CRM Patent AG (CH)

( * ) Notice: Subject to any disclaimer, the term of this patent is extended or adjusted under 35 U.S.C. 154(b) by 348 days.

(21) Appl. No.: 12/061,796

(22) Filed: Apr. 3, 2008

(65) Prior Publication Data

US 2008/0249585 A1 Oct. 9, 2008

(30) Foreign Application Priority Data

Apr. 4, 2007 (EP) .................... 07007048

(51) Int. Cl.
*A61N 1/00* (2006.01)
(52) U.S. Cl. ....................................... 607/18
(58) Field of Classification Search .............. 607/4, 607/17, 18, 37, 9, 129
See application file for complete search history.

(56) References Cited

U.S. PATENT DOCUMENTS

| | | | |
|---|---|---|---|
| 5,224,475 A | 7/1993 | Berg et al. | |
| 6,654,639 B1 | 11/2003 | Lu | |
| 2004/0260351 A1 | 12/2004 | Holmstrom et al. | |
| 2006/0142811 A1* | 6/2006 | Militello | 607/9 |
| 2007/0106359 A1* | 5/2007 | Schaer et al. | 607/129 |

FOREIGN PATENT DOCUMENTS

EP 1 459 785 A1 9/2004

* cited by examiner

*Primary Examiner*—George Manuel
*Assistant Examiner*—Robert N Wieland
(74) *Attorney, Agent, or Firm*—Craig A. Fieschko, Esq.; DeWitt Ross & Stevens S.C.

(57) ABSTRACT

A device is connected to electrode leads which performs intracardiac impedance measurements, conducts a transient pacing protocol, analyses the impedance measurements, and generates an LV lead position quality factor. The transient pacing protocol includes a repeated change ("transitions") between ventricular intrinsic rhythm and biventricular paced rhythm and may also include a variation of the atrioventricular delay (AVD) and/or the interventricular delay (VVD). The quality factor expresses the degree to which hemodynamic properties have improved due to BiV stimulation for the current LV lead position compared to intrinsic ventricular rhythm.

49 Claims, 4 Drawing Sheets

US 7,844,335 B2

IMPLANTABLE MEDICAL DEVICE AND METHOD FOR LV CORONARY SINUS LEAD IMPLANT SITE OPTIMIZATION

FIELD OF INVENTION

The invention refers to implantable medical devices (IMDs) providing improved means for pacing efficiency. The invention relates in particular to an implantable cardiac pacemaker or an implantable cardioverter/defibrillator (ICD) for bi-ventricular stimulation, and to methods for optimizing a left ventricular electrode lead site.

BACKGROUND OF THE INVENTION

For patients suffering from congestive heart failure (CHF), the synchronized stimulation of the atrium and both the right and left ventricle by an implantable pacemaker or defibrillator, called cardiac resynchronization therapy (CRT), has been shown to improve the prognosis.

For biventricular (BiV) pacing (stimulation of both ventricles of a heart), both right ventricular (RV) and left ventricular (LV) stimulation electrode leads bearing right ventricular and left ventricular stimulation electrodes are used. The LV electrode lead is implanted via the right atrium and coronary sinus into a LV cardiac vein. Often, several positions are available for the implantation site of the LV electrode lead. In order to be beneficial, the final position of the LV stimulation electrode should be optimized for hemodynamic benefit.

Pacing of the right atrium (RA), right ventricle (RV), and the left ventricle (LV) is performed by delivery of stimulation pulses to the respective heart chamber. The stimulation pulses have strength strong enough to be captured by the respective heart chamber and cause an excitation of the heart chamber's myocardium. Causing an excitation of a heart chamber that leads to contraction of said heart chamber by means of an electric stimulation pulse is called pacing the heart chamber.

Thus stimulated contractions of a heart chamber, called "pace events," and natural contractions of a heart chamber, called "intrinsic events," may occur. In a healthy heart, the natural rhythm or rate of intrinsic events is controlled by the sinus node of the heart. Therefore, the natural rhythm of intrinsic events is called "sinus rhythm" or "sinus rate".

The pacing site of the left ventricular lead for cardiac resynchronization therapy can be optimized by measuring hemodynamic parameters, which increases duration, complexity and costs of the implantation procedure.

Established methods for assessing the efficiency of biventricular pacing are listed in the following. The following methods can be used to optimize the LV lead implant position and also the pacing timing parameters:

a) noninvasive methods or those using the implanted electrodes:
  optimize electrical synchrony (ECG)
  maximum delay between RV IEGM and LV IEGM during ventricular intrinsic rhythm
  maximum plethysmographic pulse pressure during BiV stimulation
  maximum SV (Echo, Doppler echo) during BiV stimulation
  minimize mitral regurgitation (mitral insufficiency backflow doppler VTI)
  optimize mechanical synchrony (tissue doppler)
  implanted sensors (peak endocardial acceleration, RV pressure)
b) invasive measurements:
  maximum arterial pulse pressure during BiV stimulation
  maximum dp/dtmax of LV pressure during BiV stimulation
  minimum LV EDP, LAP, PCWP during BiV stimulation
  maximum SV (thermodilution, pulse contour analysis) during BiV stimulation
  optimize electrical synchrony (IEGM mapping)

The methods that reliably assess hemodynamic parameters considerably increase the effort required during implantation, since either additional equipment is needed (e.g. Echo) or invasive measurements are required (e.g. intracardiac catheter).

SUMMARY OF THE INVENTION

It is an object of the invention to provide an implantable medical device that provides an improved assessment of the efficiency of biventricular (BiV) pacing.

According to the invention, the efficiency of biventricular pacing is expressed by a quality factor.

The quality factor can be used to optimize an electrode lead position, in particular a left ventricular (LV) electrode position, or bi-ventricular pacing parameters such as an interventricular delay (VVD) or an atrioventricular delay (AVD), or both. The concept of scheduling stimulation pulses based on the delays mentioned is deemed to be general knowledge of the person skilled in the art. The same applies to the concept of demand pacing etc.

According to the present invention the object of the invention may be achieved by a heart stimulator for biventricular pacing of a heart, featuring:
  at least one stimulation pulse generator for pacing at least a left ventricle of a heart,
  an impedance determination unit for determining an intracardiac impedance value reflecting cardiac output,
  and a control unit, being connected to said stimulation pulse generator and to said impedance determination unit.

The control unit is adapted to trigger said stimulation pulse generator to generate and deliver at least left ventricular stimulation pulses when triggered and to perform a quality factor test procedure for determining a quality factor. The control unit is further adapted to determine the quality factor by comparing two impedance values.

A first intracardiac impedance value is determined for an intrinsic heart cycles sequence comprising a predetermined first number $N_{intrinsic}$ of consecutive intrinsic heart cycles wherein no left ventricular stimulation pulses are delivered. A second intracardiac impedance value is determined for a paced heart cycles sequence comprising a predetermined second number $N_{paced}$ of consecutive paced heart cycles wherein at least left ventricular stimulation pulses are delivered.

The invention is based on the idea that intracardiac impedance (Z) reflects left ventricular (LV) volume changes well and it therefore can be used as an alternative method to guide LV electrode lead positioning.

According to the invention, the hemodynamically best implantation site for the LV lead is identified by intracardiac impedance measurements using the LV lead itself and (possibly) other already implanted leads (RV lead, RA lead) and (possibly) a patch electrode. No other invasive parts are required than the device electrodes, which are implanted anyway.

For that purpose, a device (e.g., the control unit) is provided which connects to the electrode leads and—while performing the quality factor test procedure—performs intracardiac impedance measurements, conducts a certain stimulation protocol (called "transient pacing protocol"), analyzes the impedance measurements, and generates an LV lead position quality factor.

The transient pacing protocol includes a repeated change ("transitions") between ventricular intrinsic rhythm and biventricular paced rhythm and may also include a variation of the atrioventricular delay (AVD) and/or the interventricular delay (VVD).

The quality factor expresses the degree to which the hemodynamic properties have improved due to BiV stimulation for the current LV lead position compared to intrinsic ventricular rhythm. If the quality factor is determined as being the quotient of the first and the second intracardiac impedance value, a quality factor of (for example) 1.2 means that hemodynamic properties have improved by 20% over the intrinsic rhythm by BiV pacing; a quality factor <1.0 would mean that BiV pacing is hemodynamically worse than intrinsic rhythm.

Accordingly, in a preferred embodiment, the control unit is adapted to compare the first and the second impedance value by dividing the second impedance value by the first impedance value, the quotient being said quality factor.

During transient pacing, preferably impedance curves (Z-curves) are recorded.

Preferably, the control unit is adapted to calculate at least some of the parameters needed for calculation of the quality factor from the following list of parameters for both the intrinsic and the BiV pacing impedance curves of each intrinsic-BiVpacing transition, preferably using the mean or median impedance $Z_{mean}$:

EDZ: end diastolic impedance (minimum impedance in diastolic time window, may be approximated by the minimum impedance or even by $Z_{mean}$)

ESZ: end systolic impedance (maximum impedance in systolic time window, may be approximated by the maximum impedance)

SZ: ESZ-EDZ (may be approximated by the impedance amplitude or standard deviation, the maximum or minimum or maximum absolute impedance slope, or another quantity characterizing the impedance variation width)

EF: ejection fraction-like parameter, EF=SZ/ESZ, or approximated by EF=SZ/$Z_{mean}$ These parameter values are used to determine the quality factors by calculating the ratio (quotient) of these parameter values during both rhythms.

Details of determination of these parameters can be found in US 2005/0049646 and are incorporated herein by reference.

It is further preferred that the control unit calculates the quality factor by one of the following methods:

| quality factor calculation | interpretation |
| --- | --- |
| ESZ__BiV/ESZ__intr* | relative ESV reduction |
| EDZ__intr/EDZ__BiV* | relative EDV increase |
| SZ__BiV/SZ__intr | relative SV increase |
| EF__BiV/EF__intr | relative EF increase |

*Impedance Z is expected to be inversely proportional to LV volume

Alternatively the corresponding quantities may be calculated using the conductivity Y=1/Z (taking care that in the quality factors described in the first two lines of the table, the numerator and denominator change places, and EF=SY/EDY or SY/$Y_{mean}$).

The quality factor is preferably calculated separately for each intrinsic-BiVpacing transition (or each group of intrinsic-BiVpacing transitions), resulting in $N_{averages}$ values for the quality factor. The quality factors from all transition groups may then be averaged to form the one resulting quality factor for the current LV lead position (and the current AVD and VVD values).

Alternatively, the parameter values may be first averaged over all intrinsic-BiVpacing transitions, and then the quality factors may be calculated from the averaged parameters for intrinsic and for BiVpaced rhythm. This approach needs less computing power, since only one division is required for the quality factor calculation.

This device may be a stand-alone external device, or an electrophysiological tester with an integrated module performing the described tasks, or an implant programmer with an integrated part performing the described tasks, or the implant itself may perform these tasks in cooperation with the implant programmer.

Furthermore, the implant may perform this measurement independently and automatically with a programmable periodicity to check whether the LV lead position quality factor has changed, and to generate a "LV lead displacement" warning if the factor deteriorates significantly, and send the warning to a remote home monitoring service center, or warn the patient audibly.

Preferably, the intrinsic heart cycles sequence and the paced heart cycles sequence are repeated in an alternating manner for predetermined number $N_{transitions}$ of sequences.

It is further preferred that the first number $N_{intrinsic}$ of consecutive intrinsic heart cycles is larger, e.g. 2 to 5 times larger, than said second number $N_{paced}$ of consecutive paced heart cycles.

A preferred value for the first number $N_{intrinsic}$ of consecutive intrinsic heart cycles is around 15 and a preferred value for the second number $N_{paced}$ of consecutive intrinsic heart cycles is in the order of 5.

Preferably, the control unit is adapted to trigger both ventricles of a heart in each sequence of consecutive paced heart cycles.

The stimulation pulse generator is preferably connected to a coronary sinus pacing lead being adapted to be placed in the coronary sinus of a heart and bearing a left ventricular stimulation electrode at its distal end or close to its distal end. In this preferred embodiment, it is the position of the coronary sinus lead that is to be optimized.

After implantation of the RV and possibly the RA lead, the LV electrode is placed in the first position under consideration, the pacing and sensing thresholds of the implanted leads are determined and an impedance measurement sequence is started by the external device, which calculates and displays a quality factor for that position.

The physician may then decide that this position is suitable if the quality factor is sufficiently above 1.0, indicating a hemodynamic improvement over the intrinsic rhythm.

The physician may also move the LV lead to other possibly suitable positions and repeat the measurement for these positions. The position with the highest quality factor is considered as the hemodynamically best site and should be used for the final implant position of the LV lead. The external device may also provide a preferred AVD and/or VVD for that site.

With respect to impedance measurement, it is preferred that the impedance determination unit is connected to or connectable to two separate electrodes of a right ventricular pacing lead for current injection and to two separate electrodes of a left ventricular pacing lead for voltage measurement.

The impedance measurement is performed by injecting a current using two electrodes and measuring the induced voltage between two (possibly different) electrodes. The electrodes that may be chosen for the impedance measurement include the intracardiac electrodes (RA tip and ring, RV tip and coil or ring, LV distal and proximal, LA distal and proximal), the intrathoracic electrode (vena cava electrode, implant housing) and possibly additional patch electrodes attached to the patient.

The impedance preferably is measured by injecting a pulsed biphasic current and measuring the induced voltage phase synchronous. Preferably the impedance determination unit is adapted to sample the induced voltage at a rate of at least 8 Hz over a complete heart cycle or only within a systolic and a diastolic time window, determined relative to the heart timing from intracardiac electrogram (IEGM).

Preferably the current is injected between a right ventricular (RV) tip and coil (or ring) electrode and the voltage is measured between LV distal and proximal electrodes.

Details and variations of impedance measurement can be taken from U.S. Patent Application 2005/0049646, which is incorporated herein by reference.

During the impedance measurement in the course of the quality factor test procedure the control unit performs the transient pacing protocol, causing the control unit to switch several times between intrinsic ventricular rhythm and biventricular paced rhythm.

The number of consecutive paced cycles, $N_{paced}$, is preferably smaller than about 10 cycles (see below).

The number of consecutive cycles in intrinsic rhythm, $N_{intrinsic}$, is larger than the number of consecutive cycles in BiV paced rhythm, $N_{paced}$, preferably by a factor of 2 to 5. (For example, when $N_{paced}$=5, $N_{intrinsic}$=15, a transient protocol proceeds with: 5 cycles paced—15 cycles intrinsic—5 cycles paced—15 cycles intrinsic— . . . ).

The number of transient repetitions, $N_{transitions}$ (i.e. how often the rhythm changes from intrinsic to BiV stimulation) needs to be large enough that the total number of BiV paced cycles is sufficient to cover several respiration cycles (in order to be able to remove the effect of respiration on the impedance curve by averaging), preferably 4-16 repetitions.

The reason for this protocol is threefold:
1. The impedance curves for BiV pacing and intrinsic rhythm can be compared for the same LV lead position. The absolute impedance value (EDZ) and the amount of change during the heart cycle (SZ) measured is strongly dependent on the electrode position due to electrical reasons, rather than hemodynamic reasons. For that reason, it makes no sense to compare EDZ or SZ between different sites. However, the relative change of these quantities between intrinsic rhythm and BiV stimulation is expected to depend on the hemodynamic benefit due to BiV pacing at this position.
2. The hemodynamic condition of the patient changes with time, therefore a quick repeated switching between intrinsic (as a reference) and BiV paced rhythm allows to separate the (comparatively slow) changes in reference hemodynamic condition from the (immediate) effect of switching to BiV pacing. Otherwise, a change of the hemodynamic condition, which incidentally may occur just upon changing to the next lead position, could lead to incorrect conclusions.
3. Upon change to BiV pacing from intrinsic rhythm, the autonomic nervous system automatically compensates for the changed hemodynamic pumping efficiency by modulating contractility, total peripheral resistance and (if in intrinsic rhythm) atrial rate. This compensation may mask the change of pumping efficiency. Since some compensation mechanisms react within a few heart cycles, the BiV pacing sequences should be shorter than about 10 cycles.

The control unit may further be adapted to use either the heart's own intrinsic rhythm (sinus rhythm) throughout the transient pacing protocol (the right atrium is not paced by setting the basic rate of the pacemaker below the sinus rate), or, preferably, to stimulate the atrium throughout the transient protocol at a constant rate sufficiently (5-30 ppm) above the sinus rate in order to prevent a take-over by the intrinsic rhythm.

Further, the control unit can be adapted to hold an atrioventricular delay (AVD) constant while performing the transient protocol. Preferably, the AVD is sufficiently shorter than the intrinsic atrioventricular (AV) conduction time, preferably 60% of intrinsic AV conduction time.

Similarly, the control unit can be adapted to hold an interventricular delay (VVD) constant during performing the transient protocol, preferably at about 0 ms.

As pointed out above, in preferred embodiment, the control unit may be adapted to implicitly optimize the atrioventricular delay AVD and/or the interventricular delay VVD for bi-ventricular pacing.

To achieve such implicit AVD and/or VVD optimization, the control unit is preferably adapted to perform the described transient pacing protocol at each LV lead site several times for a set of atrioventricular delays (all shorter than intrinsic conduction) and take the best quality factor found as quality factor for that position. Since this represents an implicit AVD optimization for each test-site, the AVD values corresponding to the best quality factor can be stored in memory for each LV lead position (in order to be suggested for programming the AVD after final lead positioning).

Similarly, the control unit may be adapted to perform the described transient pacing protocol at each LV lead site several times for a set of interventricular delays (VVDs) and take the best quality factor found as quality factor for that position. Since this represents an implicit VVD optimization for each test-site, the VVD values corresponding to the best quality factor can be stored in memory for each LV lead position (in order to be suggested for programming the VVD after final lead positioning).

Both AVD and VVD variation may by combined by first varying the AVD, then using the AVD with the best quality factor and performing the pacing protocol again with variation of the VVD.

With respect to impedance analysis, it is preferred that the control unit is adapted to calculate two averaged impedance curves (Z-curves) for each intrinsic to BiV paced transition:
one from the $N_{paced}$ cycles of the BiV paced rhythm after the transition, and
one from the $N_{reference}$ intrinsic cycles immediately before the transition $$N_{reference} = N_{paced}$$

Thus, a number of ($N_{intrinsic} - N_{reference}$) intrinsic cycles following the BiV paced cycles are discarded. As an example, $N_{paced}$=5, $N_{intrinsic}$=15, $N_{reference}$=5 (i.e., 10 intrinsic cycles are not included in the analysis).

For calculating averaged impedance curves, the ventricular event from the IEGM or pacemaker timing is used for synchronization.

This results in $N_{averages} = N_{transitions}$ pairs of averaged impedance curves. Alternatively also $N_{group}$=2 or 4 subsequent transitions may be grouped for the calculation of averaged impedance curves (resulting in $N_{averages} = N_{transitions}/2$ or $N_{transitions}/4$ pairs of averaged impedance curves).

Additionally the resulting averaged curves may be processed using the following methods:
smoothing
removal of known technically caused artefacts
removal of artefacts caused by the ventricular IEGM
curve fitting The preprocessed Z-curves are analyzed and one or several parameters are extracted that characterize certain attributes of the impedance curve (separately for the $N_{averages}$ BiVpaced curves and intrinsic curves).

It is to be appreciated that features of preferred embodiments of the invention may be combined in any useful manner thus arriving at further embodiments of the invention not explicitly mentioned in this disclosure.

BRIEF DESCRIPTION OF THE DRAWINGS

The foregoing and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

DESCRIPTION OF THE PREFERRED EMBODIMENT

Figure 1:
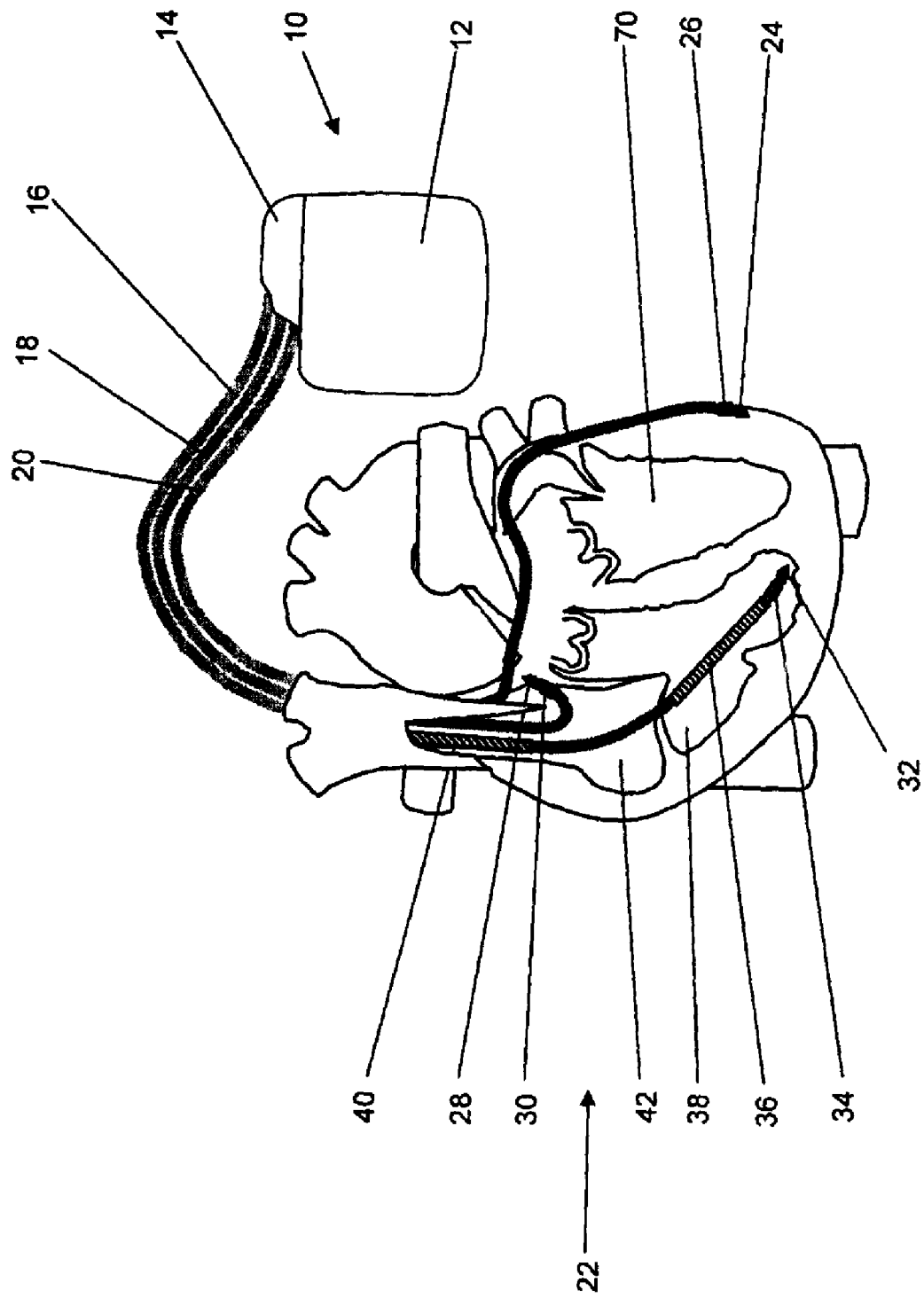
FIG. 1 shows a dual chamber pacemaker/atrial defibrillator/cardioverter connected to electrode leads placed in a heart.

From FIG. 1 it is apparent that stimulator 10 comprises a case 12 and header 14.

The heart stimulator 10 is connected to three electrode leads, namely a right ventricular electrode lead 16, a right atrial electrode lead 18 and a left ventricular electrode lead 20. The left ventricular electrode lead 20 is designed to pass through the coronary sinus of heart 22. A typical electrode suitable for use with heart stimulator 10 is the electrode lead corox+UP/BB (Biotronik).

Left ventricular electrode lead 20 comprises a left ventricular tip electrode 24 at the distal end of the left ventricular electrode lead 20 and a left ventricular ring electrode 26.

Atrial electrode lead 18 comprises a right atrial tip electrode 28 at the distal end of the right atrial electrode lead 18 and a right atrial ring electrode 30.

The right ventricular electrode lead 16 comprises right ventricular tip electrode 32 at the distal end of the right ventricular electrode lead 16 and a right ventricular ring electrode 34.

In order to illustrate that heart stimulator 10 may be adapted to act as an implantable cardioverter/defibrillator (ICD) ventricular electrode lead 16 also includes a ventricular shock coil 36 for the delivery of defibrillation shocks to the right ventricle 38 of the heart 22 and an atrial shock coil 40 for the delivery of atrial defibrillation shocks to a right atrium 42 of the heart 22.

Each electrode and shock coil of electrode leads 16 to 20 is separately connected to an electric circuit enclosed by case 12 of heart stimulator 10 by way of electrical contacts of a plaque (not shown) at the proximal end of each electrode lead 16 to 20 and corresponding contacts (not shown) in header 14 of heart stimulator 10.

Figure 2:
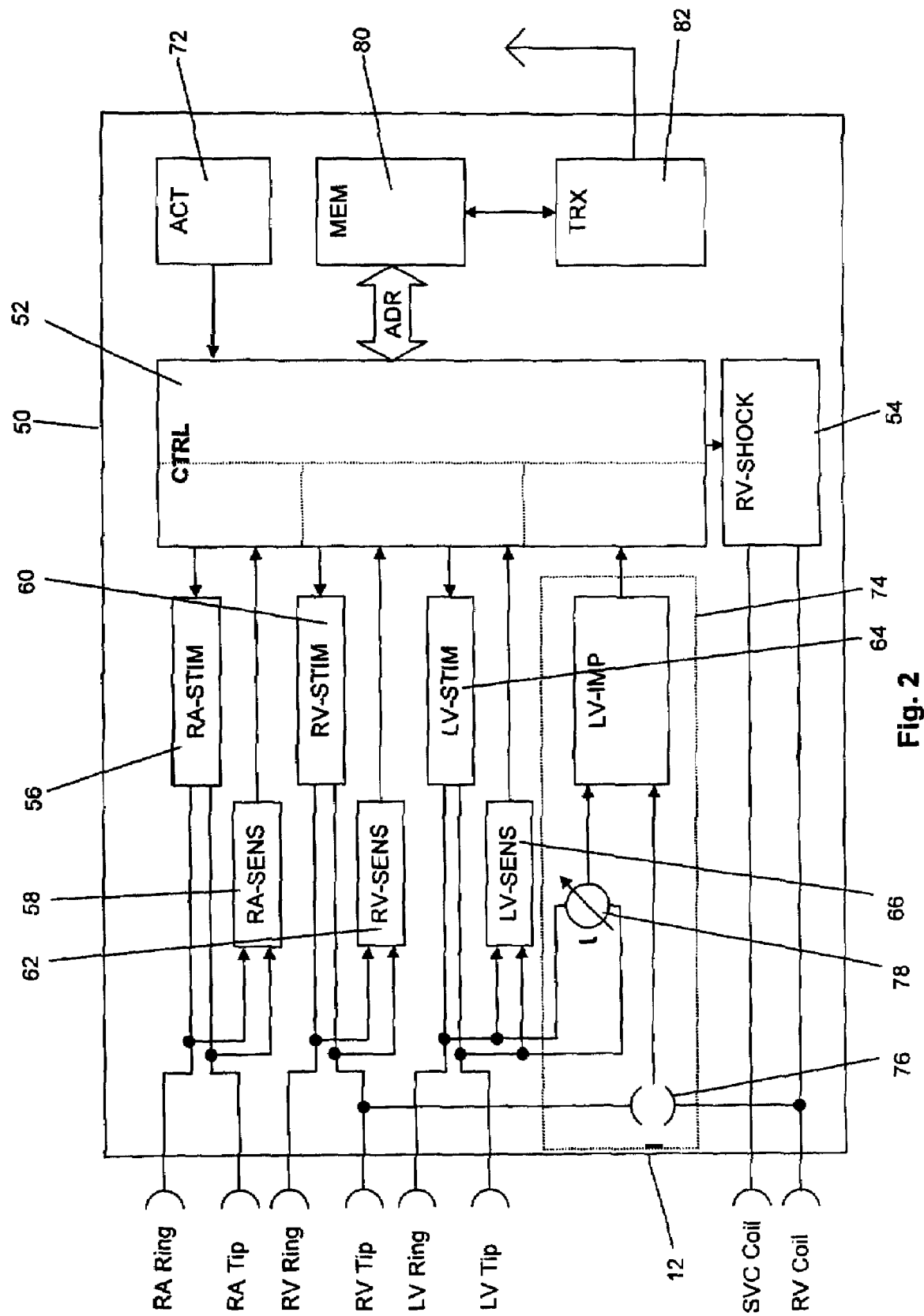
FIG. 2 is a schematic block diagram of the heart stimulator of FIG. 1.

Right atrial shock coil 40 is connected to right atrial shock generator 50 (see FIG. 2) that is controlled by a control unit 52 of heart stimulator 10.

Similarly right ventricular shock coil 36 is connected to a right ventricular shock generator 54 that is also connected to control unit 52.

Right atrial tip electrode 28 and right atrial ring electrode 30 are both connected to right atrial stimulation pulse generator 56 and to a right atrial sensing stage 58 that are in turn connected to control unit 52.

Right atrial stimulation pulse generator 56 is adapted to generate atrial stimulation pulses of sufficient strength to cause an excitation of atrial myocardium by an electrical stimulation pulse delivered via right atrial tip electrode 28 and right atrial ring electrode 30. Preferably, means are provided to adapt the right atrial stimulation pulse strength to the stimulation threshold.

Right atrial sensing stage 58 is adapted to pick up myocard cardial potentials indicating an intrinsic atrial excitation that corresponds to a natural atrial contraction. By way of right atrial sensing stage 58, it is possible to stimulate the right atrium 42 of heart 22 in a demand mode wherein a right atrial stimulation pulse is inhibited if an intrinsic atrial event (intrinsic atrial excitation) is sensed by right atrial sensing stage 58 prior to expiration of an atrial escape interval.

In a similar manner, right ventricular ring electrode 34 and right ventricular tip electrode 32 are connected to a right ventricular stimulation pulse generator 60 and to a right ventricular sensing stage 62 that in turn are connected to control unit 52. By way of right ventricular tip electrode 32, right ventricular ring electrode 34, right ventricular stimulation generator 60 and right ventricular sensing stage 62, right ventricular stimulation pulses can be delivered in a demand mode to the right ventricle 38 of heart 22.

In the same way left ventricular tip electrode 32 and left ventricular ring electrode 26 are connected to the left ventricular stimulation pulse generator 64 and the left ventricular sensing stage 66 that are in turn connected to control unit 52 to allow for stimulation of a left ventricle 70 of heart 22.

Triggering and inhibition of delivery of stimulation pulses to the right atrium, the right ventricle or the left ventricle is controlled by control unit 52, in a manner known to the skilled artisan. The timing that schedules delivery of stimulation pulses if needed is controlled by a number of intervals which may at least partly depend on a hemodynamic demand of a patient that is sensed by means of an activity sensor 72 connected to control unit 52. Activity sensor 72 allows for rate adaptive pacing wherein a pacing rate (the rate of consecutive ventricular stimulation pulses for a duration of consecutive atrial stimulation pulses) depends on a physiological demand of a patient that is sensed by the activity sensor 72. Details of rate adaptation are known to the skilled artisan and need not to be explained in detail in this description.

Whereas an actual stimulation rate determines the timing from one (paced) heart cycle to another, intervals like an atrioventricular delay interval and an interventricular delay interval determine the timing within one heart cycle. Starting with an atrial event, the right ventricle would be excited (either intrinsically or paced) at the end of an atrioventricular delay interval. A left ventricular contraction should follow the right ventricular contraction at the end of an interventricular delay interval. This includes the case wherein the right ventricle and the left ventricle are excited at the same time, resulting in an interventricular delay interval duration of zero. Also, it is possible that the left ventricle may be excited prior to the right ventricle resulting in an negative interventricular delay interval duration.

In any case, the atrioventricular delay interval duration and the interventricular delay interval duration need to be adapted to an individual heart in order to achieve an optimized cardiac output.

Heart stimulator 10 is adapted to determine an optimal atrioventricular delay interval duration and an optimal interventricular delay interval duration automatically.

For this purpose, heart stimulator 10 includes an impedance determination unit 74 that includes a constant current source 76 and a voltage measuring unit 78. The constant current source 74 generates a pulsed biphasic current that comprises pairs of current pulses that have an alternating polarity and the same absolute current strength. An impedance determination stage 80 calculates an impedance value based on the current strength and the voltage measured. As will be appreciated by the skilled artisan, instead of measuring the impedance, the inverse value of the impedance, equivalent values such as male conductivity or conductance, respectively, can be used throughout the invention in an analogous manner taking into account the inverse relationship.

Control unit 40 is adapted to determine a quality factor that represents the efficiency of biventricular pacing. In order to determine the quality factor, impedance measurements are performed while applying a transient pacing protocol controlled by the control unit 40.

The transient pacing protocol causes the control unit to switch several times between intrinsic ventricular rhythm (no triggering of stimulation pulses for a number of $N_{intrinsic}$ heart cycles) and biventricular paced rhythm.

The number of consecutive paced cycles, $N_{paced}$, is preferably smaller than 10 cycles (see below).

The number of consecutive cycles in intrinsic rhythm, $N_{intrinsic}$, is larger than the number of consecutive cycles in BiV paced rhythm, $N_{paced}$, preferably by a factor of 2 to 5. (For example, where $N_{paced}$=5, $N_{intrinsic}$=15, a transient protocol may take the form: 5 cycles paced—15 cycles intrinsic—5 cycles paced—15 cycles intrinsic— . . . ).

The number of transient repetitions, $N_{transition}$, (i.e. how often the rhythm changes from intrinsic to BiV stimulation) needs to be large enough that the total number of BiV paced cycles is sufficient to cover several respiration cycles (in order to be able to remove the effect of respiration on the impedance curve by averaging), preferably 4 to 16 repetitions.

To achieve an implicit AVD and/or VVD optimization, the control unit is adapted to perform the described transient pacing protocol at each LV lead site several times for a set of atrioventricular delays (all shorter than intrinsic conduction) and take the best quality factor found as quality factor for that position. Since this represents an implicit AVD-optimization for each test-site, the AVD values corresponding to the best quality factor can be memorized for each LV lead position so that they may be used for programming the AVD after final lead positioning.

Similarly, the control unit is adapted to perform the described transient pacing protocol at each LV lead site several times for a set of interventricular delays (VVD's) and take the best quality factor found as quality factor for that position. Since this represents an implicit VVD optimization for each test-site, the VVD values corresponding to the best quality factor can be memorized for each LV lead position so that they may be used for programming the VVD after final lead positioning.

Both AVD and VVD variation are combined by first varying the AVD, then using the AVD with the best quality factor and performing the pacing protocol again with variation of the VVD.

Alternatively, in a more simple embodiment, both the atrioventricular delay (AVD) and the interventricular delay (VVD) can be held constant. Then, the atrioventricular delay (AVD) is sufficiently shorter than the intrinsic atrioventricular (AV) conduction time, preferably about 60% of intrinsic AV conduction time. The interventricular delay (VVD) preferably is about 0 ms.

During performing the transient pacing protocol either sinus rhythm is used throughout (the right atrium is not paced by setting the basic rate of the pacemaker below the sinus rate), or, preferably, the atrium is stimulated throughout the transient protocol at a constant rate (5-30 ppm) sufficiently above the sinus rate in order to prevent a take-over by the intrinsic rhythm.

For each intrinsic to BiV paced transition, two averaged impedance curves are calculated:
  one from the $N_{paced}$ cyles of the BiV paced rhythm after the transition, and
  one from the $N_{reference}$ intrinsic cycles immediately before the transition $N_{reference}$=$N_{paced}$ Thus, a number of ($N_{intrinsic}$–$N_{reference}$) intrinsic cycles following the BiV paced cycles are discarded. As a preferred example, $N_{paced}$=5, $N_{intrinsic}$=15, $N_{reference}$=5 (i.e., 10 intrinsic cycles are not included in the analysis).

The control is further adapted to calculate averaged impedance curves (Z-curves) while performing the transient pacing protocol as follows:

For calculating averaged impedance curves, the ventricular event from the IEGM or pacemaker timing is used for synchronization.

This results in $N_{averages}$=$N_{transitions}$ pairs of averaged impedance curves. Alternatively also $N_{group}$=2 or 4 subsequent transitions may be grouped for the calculation of averaged impedance curves (resulting in $N_{averages}$=$N_{transitions}$/2 or $N_{transitions}$/4 pairs of averaged impedance curves).

Additionally the resulting averaged curves may be processed using the following methods:
  smoothing
  removal of known technically caused artifacts
  removal of artifacts caused by the ventricular IEGM
  curve fitting The preprocessed Z-curves are analyzed and one or several parameters are extracted, that characterize certain attributes of the impedance curve (separately for the Naverages BiV-paced curves and intrinsic curves).

Preferably a subset (that is needed for calculation of the quality factor) from the following list of parameters is calculated for both the intrinsic and the BiV impedance curves of each intrinsic-BiV pacing transition:
  $Z_{mean}$: the mean or median impedance
  EDZ: end diastolic impedance (minimum impedance in diastolic time window, may also be approximated by the minimum impedance or even by $Z_{mean}$)

ESZ: end systolic impedance (maximum impedance in systolic time window, may also be approximated by the maximum impedance)

SZ: ESZ-EDZ (may also be approximated by the impedance amplitude or standard deviation, the maximum or minimum or maximum absolute impedance slope, or another quantity characterizing the impedance variation width)

EF: ejection fraction-like parameter, EF=SZ/ESZ, or approximated by $EF=SZ/Z_{mean}$ These parameter values are used by the control unit to determine the quality factors by calculating the ratio (quotient) of these parameter values during both rhythms.

Preferably the quality factor is calculated by one of the following methods:

| quality factor calculation | interpretation |
| --- | --- |
| ESZ_BiV/ESZ_intr* | relative ESV reduction |
| EDZ_intr/EDZ_BiV* | relative EDV increase |
| SZ_BiV/SZ_intr | relative SV increase |
| EF_BiV/EF_intr | relative EF increase |

*Impedance Z is expected to be inversely proportional to LV volume

Alternatively the corresponding quantities may be calculated using the conductivity Y=1/Z (taking care that in the quality factors described in the first two lines of the table numerator and denominator change places, and EF=SY/EDY or $SY/Y_{mean}$).

The quality factor is now calculated separately for each intrinsic-BiVpacing transition (or each group of intrinsic-BiVpacing transitions), resulting in $N_{averages}$ values for the quality factor. The quality factors from all transition groups are then averaged to form the one resulting quality factor for the current LV lead position (and the current AVD and VVD values).

Figure 3:
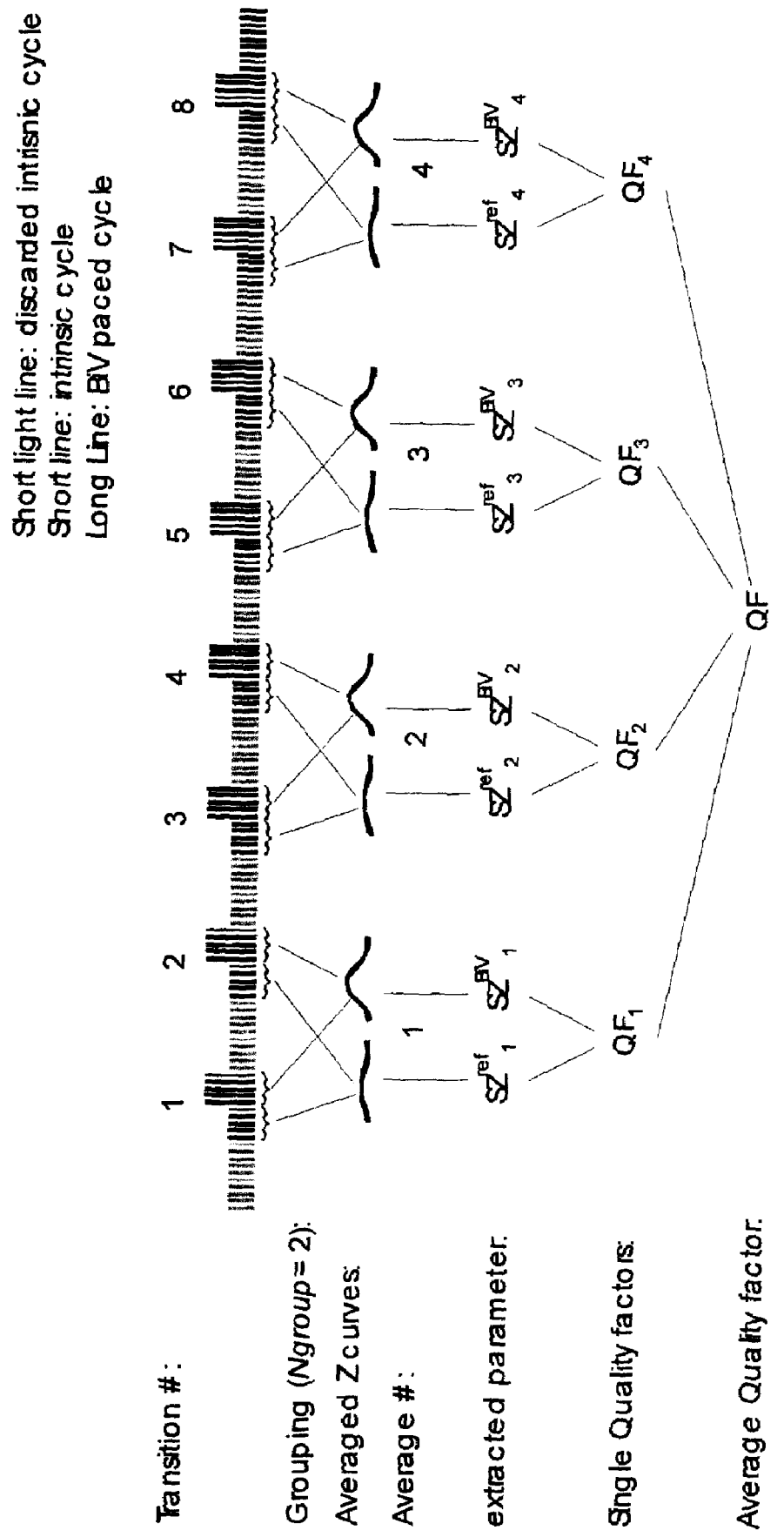
FIG. 3 is a schematic overview of the impedance analysis from the heart cycles to the quality factor for one LV lead position without AVD or VVD variation (for Nintrinsic=15, Nreference=5, Npaced=5, Ntransitions=8, Ngroup=2, Naverages=4, extracted parameter=SZ)
Figure 4:
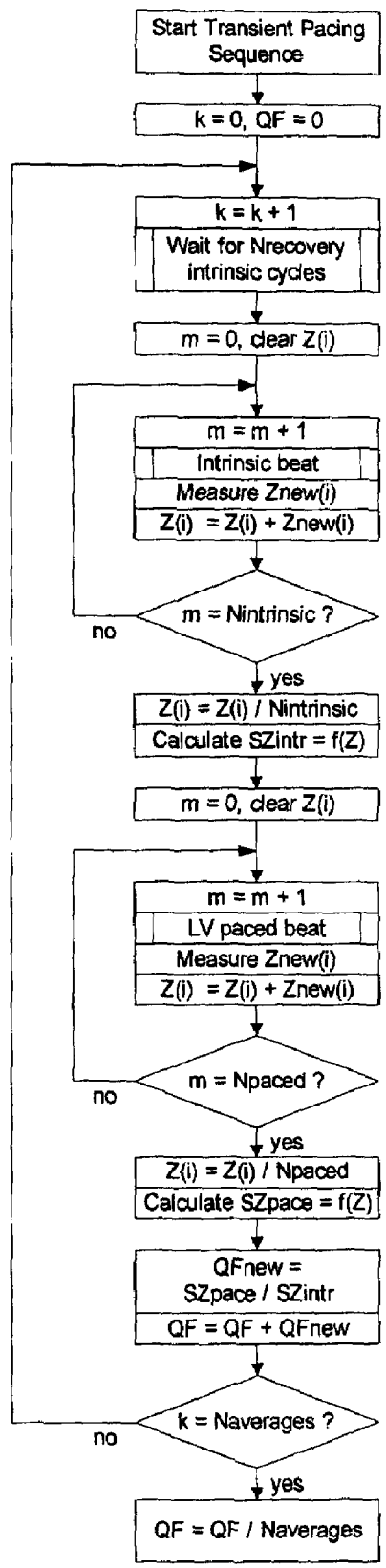
FIG. 4 is a flow chart illustrating the quality factor determination by the heart stimulator of FIG. 2.

A schematic overview of the impedance analysis (for $N_{intrinsic}=15$, $N_{reference}=5$, $N_{paced}=5$, $N_{transitions}=8$, $N_{group}=2$, $N_{averages}=4$, extracted parameter=SZ) is shown in FIG. 3.

Alternatively, the parameter values may be first averaged over all intrinsic-BiVpacing transitions, and then the quality factors may be calculated from the averaged parameters for intrinsic and for BiVpaced rhythm. This approach needs less computing power; since only one division is required for the quality factor calculation.

Although an exemplary embodiment of the present invention has been shown and described, it should be apparent to those of ordinary skill that a number of changes and modifications to the invention may be made without departing from the spirit and scope of the invention. In particular, it is possible to implement the features of the claimed transceiver unit into state of the art implantable medical devices such as implantable pacemakers or implantable cardioverter/defibrillator. This invention can readily be adapted to such devices by following the present teachings. All such changes, modifications and alterations should therefore be recognized as falling within the scope of the present invention.

What is claimed is:

1. A heart stimulator for biventricular pacing of a heart, comprising:
   a. at least one stimulation pulse generator for pacing at least a left ventricle of a heart,
   b. an impedance determination unit for determining an intracardiac impedance value reflecting cardiac output,
   c. a control unit connected to the stimulation pulse generator and to the impedance determination unit, the control unit being adapted to:
      (1) trigger the stimulation pulse generator to generate and deliver at least left ventricular stimulation pulses when triggered, and
      (2) perform a quality factor test procedure for determining a quality factor, wherein:
         (a) a first intracardiac impedance value or impedance curve is determined for an intrinsic heart cycles sequence comprising a predetermined first number $N_{intrinsic}$ of consecutive intrinsic heart cycles wherein no left ventricular stimulation pulses are delivered,
         (b) a second intracardiac impedance value or impedance curve is determined for a paced heart cycles sequence comprising a predetermined second number $N_{paced}$ of consecutive paced heart cycles wherein at least left ventricular stimulation pulses are delivered, and
         (c) the first and second intracardiac impedance values or curves are compared to each other.

2. The heart stimulator of claim 1 wherein the control unit is adapted to compare the first and the second intracardiac impedance values or curves by obtaining a quality factor dependent on the second impedance value or curve divided by the first impedance value or curve.

3. The heart stimulator of claim 1 wherein the intrinsic heart cycles sequence and the paced heart cycles sequence are repeated in an alternating manner for a predetermined number $N_{transitions}$ of sequences.

4. The heart stimulator of claim 3 wherein the number $N_{transitions}$ of sequences is 4 to 16.

5. The heart stimulator of claim 1 wherein the first number $N_{intrinsic}$ of consecutive intrinsic heart cycles is larger than the second number $N_{paced}$ of consecutive paced heart cycles.

6. The heart stimulator of claim 5 wherein the first number $N_{intrinsic}$ of consecutive intrinsic heart cycles is 2 to 5 times larger than the second number $N_{paced}$ of consecutive paced heart cycles.

7. The heart stimulator of claim 5 wherein the first number $N_{intrinsic}$ of consecutive intrinsic heart cycles is at or near 15.

8. The heart stimulator of claim 5 wherein the second number $N_{paced}$ of consecutive intrinsic heart cycles is at or near 5.

9. The heart stimulator of claim 1 wherein the control unit is adapted to trigger both right and left ventricular stimulation pulses in each sequence of consecutive paced heart cycles.

10. The heart stimulator of claim 1 wherein the control unit is adapted to use an intrinsic rhythm throughout the quality factor test procedure, wherein the right atrium is not paced by setting the basic rate of the triggering of ventricular stimulation pulses below the intrinsic rate.

11. The heart stimulator of claim 1 wherein the control unit is adapted to stimulate the atrium throughout the quality factor test procedure at a constant rate sufficiently above an intrinsic rate that a take-over by the intrinsic rhythm is prevented.

12. The heart stimulator of claim 1 wherein the control unit is adapted to hold an atrioventricular delay (AVD) constant while performing the quality factor test procedure.

13. The heart stimulator of claim 12 wherein the AVD is shorter than the intrinsic atrioventricular (AV) conduction time.

14. The heart stimulator of claim 1 wherein the control unit is adapted to hold an interventricular delay (VVD) constant during performing the quality factor test procedure.

15. The heart stimulator of claim 14 wherein the VVD is 0 ms.

16. The heart stimulator of claim 1 wherein the control unit is adapted to implicitly optimize an atrioventricular delay (AVD) and/or an interventricular delay (VVD) for bi-ventricular pacing.

17. The heart stimulator of claim 16 wherein the control unit is adapted to:
a. perform the quality factor test procedure several times for a set of atrioventricular delays (AVDs) that are all shorter than an intrinsic atrioventricular conduction time, and
b. store the AVD related to the best quality factor found as an optimum AVD.

18. The heart stimulator of claim 17 wherein the control unit is adapted to:
a. first vary the atrioventricular delay (AVD),
b. then use the AVD with the best quality factor, and
c. perform the quality factor test procedure again with variation of the interventricular delay (VVD).

19. The heart stimulator of claim 16 wherein the control unit is adapted to:
a. perform the quality factor test procedure several times for a set of interventricular delays (VVDs), and
b. store the VVD related to the best quality factor found as an optimum VVD.

20. The heart stimulator of claim 1 wherein the control unit is adapted to calculate two averaged impedance curves (Z-curves), one for an intrinsic heart cycles sequence and the other for a paced heart cycles sequence.

21. The heart stimulator of claim 20 wherein the control unit is adapted to calculate:
a. one Z-curve from the $N_{paced}$ cycles of the paced heart cycles sequence after a transition from the intrinsic heart cycles sequence to the paced heart cycles sequence, and
b. one Z-curve from the $N_{reference}$ intrinsic cycles immediately before the transition from the intrinsic heart cycles sequence to the paced heart cycles sequence.

22. The heart stimulator of claim 21 wherein $N_{reference}$ equals $N_{paced}$.

23. The heart stimulator of claim 1 wherein the control unit is adapted to use points of time of ventricular events taken from an intracardiac electrogram (IEGM) for synchronization of impedance curves to be averaged.

24. The heart stimulator of claim 1 wherein the stimulation pulse generator is connected to a coronary sinus pacing lead placed in the coronary sinus of a heart and bearing a left ventricular stimulation electrode at or near its distal end.

25. The heart stimulator of claim 1 wherein the impedance determination unit is connected to:
a. two separate electrodes of a right ventricular pacing lead for current injection, and
b. two separate electrodes of a left ventricular pacing lead for voltage measurement.

26. A biventricular heart stimulator having
a. at least one stimulation pulse generator connected to a right ventricular stimulation electrode lead and a left ventricular electrode lead, and being adapted to generate right ventricular stimulation pulses and left ventricular stimulation pulses,
b. a control unit connected to the stimulation pulse generator and being adapted to trigger right ventricular stimulation pulses and left ventricular stimulation pulses, wherein:
(1) a left ventricular stimulation pulse follows a right ventricular stimulation pulse after expiry of a positive interventricular delay interval (VVD) that is started with triggering of a right ventricular stimulation pulse, or
(2) a right ventricular stimulation pulse follows a left ventricular stimulation pulse after expiry of a negative interventricular delay interval (VVD) that is started with triggering of a left ventricular stimulation pulse, the interventricular delay interval (VVD) being adjustable, and
c. an intracardiac impedance or conductivity measuring stage connected to the control unit and being adapted to put out a time varying signal corresponding the time course of the intracardiac impedance or conductivity, wherein:
A. the intracardiac impedance or conductivity measuring stage is adapted to generate:
i. a right ventricular impedance signal representing the time course of the right ventricular impedance or conductivity, and
ii. a left ventricular impedance signal representing the time course of the left ventricular impedance or conductivity, and
B. the control unit is adapted to perform a quality factor test procedure for determining a quality factor, wherein
i. a first intracardiac impedance value is determined for an intrinsic heart cycles sequence comprising a predetermined first number $N_{intrinsic}$ of consecutive intrinsic heart cycles wherein no left ventricular stimulation pulses are delivered,
ii. a second intracardiac impedance value is determined for a paced heart cycles sequence comprising a predetermined second number $N_{paced}$ of consecutive paced heart cycles wherein at least left ventricular stimulations pulses are delivered, and
iii. the two impedance values thus determined are compared to each other,
C. the control unit is further adapted to:
i. perform the quality factor test procedure several times for a set of atrioventricular delays that are all shorter than an intrinsic atrioventricular conduction time,
ii. store the AVD related to the best quality factor found as an optimum AVD,
iii. perform the quality factor test procedure several times for a set of interventricular delays (VVDs) while using the optimum AVD, and
iv. store the VVD related to the best quality factor found as an optimum VVD.

27. A method of optimizing a left ventricular stimulation electrode site, the method comprising the steps of:
a. determining a quality factor representative of the efficiency of biventricular pacing, the determination of the quality factor including a quality factor test procedure having the steps of:
(1) determining a first intracardiac impedance value or impedance curve for an intrinsic heart cycles sequence comprising a predetermined first number $N_{intrinsic}$ of consecutive intrinsic heart cycles wherein no left ventricular stimulation pulses are delivered,
(2) determining a second intracardiac impedance value or impedance curve for a paced heart cycles sequence comprising a predetermined second number $N_{paced}$ of consecutive paced heart cycles wherein at least left ventricular stimulations pulses are delivered, and
(3) comparing the determined impedance values or curves to each other,
b. moving the left ventricular stimulation electrode,
c. redetermining the quality factor, and
d. comparing the determined quality factors.

28. The method of claim 27 wherein the quality factor is dependent on the second impedance value or curve divided by the first impedance value or curve.

29. The method of claim 27 wherein determination of the quality factor includes repeating the intrinsic heart cycles sequence and the paced heart cycles sequence in an alternating manner for predetermined number $N_{transitions}$ of sequences.

30. The method of claim 29 wherein the number $N_{transitions}$ of sequences is 4 to 16.

31. The method of claim 27 wherein the first number $N_{intrinsic}$ of consecutive intrinsic heart cycles is larger than the second number $N_{paced}$ of consecutive paced heart cycles.

32. The method of claim 31 wherein the first number $N_{intrinsic}$ of consecutive intrinsic heart cycles is 2 to 5 times larger than the second number $N_{paced}$ of consecutive paced heart cycles.

33. The method of claim 31 wherein the first number $N_{intrinsic}$ of consecutive intrinsic heart cycles is at or about 15.

34. The method of claims 31 wherein the second number $N_{paced}$ of consecutive intrinsic heart cycles is at or about 5.

35. The method of claim 27 wherein determination of the quality factor further comprises triggering both right and left ventricular stimulation pulses in each sequence of consecutive paced heart cycles.

36. The method of claim 27 wherein determination of the quality factor further comprises using an intrinsic rhythm throughout the quality factor test procedure, wherein the right atrium is not paced by setting the basic rate of the triggering of ventricular stimulation pulses below the intrinsic rate.

37. The method of claim 27 wherein determination of the quality factor further comprises stimulating the atrium throughout the quality factor test procedure at a constant rate which is sufficiently above an intrinsic rate to prevent a takeover by the intrinsic rhythm.

38. The method of claim 27 wherein determination of the quality factor further comprises holding an atrioventricular delay (AVD) constant while performing the quality factor test procedure.

39. The method of claim 38 wherein the atrioventricular delay (AVD) is shorter than the intrinsic atrioventricular (AV) conduction time.

40. The method of claim 27 wherein determination of the quality factor further comprises holding an interventricular delay (VVD) constant during performing the quality factor test procedure.

41. The method of claim 40 wherein the interventricular delay (VVD) is 0 ms.

42. The method of claim 27 wherein determination of the quality factor further comprises optimizing an atrioventricular delay AVD and/or an interventricular delay VVD for bi-ventricular pacing.

43. The method of claim 42 further comprising:
a. performing the quality factor test procedure several times for a set of atrioventricular delays (AVDs) that are all shorter than an intrinsic atrioventricular conduction time, and
b. storing the AVD related to the best quality factor found as an optimum AVD.

44. The method of claim 43 further comprising:
a. first varying the AVD,
b. using the AVD with the best quality factor, and
c. performing the quality factor test procedure again with variation of the VVD.

45. The method of claim 42 further comprising:
a. performing the quality factor test procedure several times for a set of interventricular delays (VVDs), and
b. storing the VVD related to best quality factor found as an optimum VVD.

46. The method of claim 27 wherein determination of the quality factor further comprises calculating two averaged impedance curves (Z-curves), one for an intrinsic heart cycles sequence and the other for a paced heart cycles sequence.

47. The method of claim 46 wherein calculating two averaged impedance curves further comprises using points of time of ventricular events taken from an intracardiac electrogram (IEGM) for synchronization of impedance curves to be averaged.

48. The method of claim 27 further comprising calculating:
a. a Z-curve from the $N_{paced}$ cycles of the paced heart cycles sequence after a transition from the intrinsic heart cycles sequence to the paced heart cycles sequence, and
b. a Z-curve from the $N_{reference}$ intrinsic cycles immediately before the transition from the intrinsic heart cycles sequence to the paced heart cycles sequence.

49. The method of claim 47 wherein $N_{reference}$ equals $N_{paced}$.

* * * * *